United States Patent [19]

Ruka et al.

[11] Patent Number: 5,498,487

[45] Date of Patent: Mar. 12, 1996

[54] OXYGEN SENSOR FOR MONITORING GAS MIXTURES CONTAINING HYDROCARBONS

[75] Inventors: Roswell J. Ruka; Richard A. Basel, both of Pittsburgh, Pa.

[73] Assignee: Westinghouse Electric Corporation, Pittsburgh, Pa.

[21] Appl. No.: 288,850

[22] Filed: Aug. 11, 1994

[51] Int. Cl.$^6$ .................................................. H01M 8/18
[52] U.S. Cl. ................................. 429/20; 429/17; 429/30; 429/31; 429/32; 429/34; 429/40; 429/41
[58] Field of Search ............................. 429/30, 31, 32, 429/34, 40, 41, 17, 20; 204/421, 424, 427

[56] References Cited

U.S. PATENT DOCUMENTS

| | | | |
|---|---|---|---|
| Re. 28,792 | 4/1976 | Ruka et al. | 204/1 |
| 3,400,054 | 9/1968 | Ruka et al. | 204/1 |
| 4,138,881 | 2/1979 | Isenberg | 73/27 R |
| 4,322,383 | 3/1982 | Yasuda et al. | 422/95 |
| 4,377,460 | 3/1983 | Hirayama et al. | 204/195 S |
| 4,378,691 | 4/1983 | Terada et al. | 73/27 R |
| 4,391,690 | 7/1983 | Lin et al. | 204/412 |
| 4,395,468 | 7/1983 | Isenberg | 429/31 |
| 4,490,444 | 12/1984 | Isenberg | 429/31 |
| 4,728,882 | 3/1988 | Stanbro et al. | 324/61 R |
| 4,729,931 | 3/1988 | Grimble | 429/17 |
| 4,810,529 | 3/1989 | Mantese et al. | 427/123 |
| 4,898,792 | 2/1990 | Singh et al. | 429/30 |
| 4,902,401 | 2/1990 | Lin et al. | 204/427 |
| 4,983,471 | 1/1991 | Reichner et al. | 429/19 |
| 5,047,299 | 9/1991 | Shockling | 429/20 |
| 5,082,751 | 1/1992 | Reichner | 429/19 |
| 5,137,616 | 8/1992 | Poor et al. | 204/427 |
| 5,143,800 | 9/1992 | George et al. | 429/34 |
| 5,169,730 | 12/1992 | Reichner | 429/20 |

OTHER PUBLICATIONS

Weissbart, et al., "Oxygen Gauge", The Review of Scientific Instruments, vol. 32, No. 5, 593–595, May, 1961.

Primary Examiner—Bruce F. Bell

[57] ABSTRACT

A gas sensor measures $O_2$ content of a reformable monitored gas containing hydrocarbons $H_2O$ and/or $CO_2$, preferably in association with an electrochemical power generation system. The gas sensor has a housing communicating with the monitored gas environment and carries the monitored gas through an integral catalytic hydrocarbon reforming chamber containing a reforming catalyst, and over a solid electrolyte electrochemical cell used for sensing purposes. The electrochemical cell includes a solid electrolyte between a sensor electrode that is exposed to the monitored gas, and a reference electrode that is isolated in the housing from the monitored gas and is exposed to a reference gas environment. A heating element is also provided in heat transfer communication with the gas sensor. A circuit that can include controls operable to adjust operations via valves or the like is connected between the sensor electrode and the reference electrode to process the electrical signal developed by the electrochemical cell. The electrical signal varies as a measure of the equilibrium oxygen partial pressure of the monitored gas. Signal noise is effectively reduced by maintaining a constant temperature in the area of the electrochemical cell and providing a monitored gas at chemical equilibria when contacting the electrochemical cell. The output gas from the electrochemical cell of the sensor is fed back into the conduits of the power generating system.

9 Claims, 3 Drawing Sheets

* THEORETICAL NERNST POTENTIAL AT 936°C, 0.97 ATM TOTAL PRESSURE, AIR AT REFERENCE ELECTRODE (~21% $O_2$), REFORMER INLET TO METHANE MOLE RATIO O:C AS INDICATED IN FIGURE 2.

OXYGEN SENSOR FOR MONITORING GAS MIXTURES CONTAINING HYDROCARBONS

GOVERNMENT CONTRACT

The Government of the United States of America has rights in the invention pursuant to Cooperative Agreement DE-AC21-80ET-17089 of the United States Department of Energy.

BACKGROUND OF THE INVENTION

FIELD OF THE INVENTION

The invention relates to the field of catalytic hydrocarbon gas reformers, and more particularly to an oxygen gauge which assists in monitoring ratios of $H_2O$ (steam) to gaseous hydrocarbon, or in other words oxygen to carbon (O:C), in a hydrocarbon feed gas stream entering or leaving a hydrocarbon gas reformer of an electrochemical fuel cell generator, such as a high temperature, solid oxide electrolyte, fuel cell generator.

Natural gas, for example comprising methane ($CH_4$), ethane ($C_2H_6$), propane ($C_3H_8$), butane ($C_4H_{10}$) and nitrogen ($N_2$), vaporized petroleum fractions such as naphtha, and also alcohols such as ethyl alcohol ($C_2H_5OH$), are appropriate fuels for an electrochemical generator apparatus, such as a high temperature, solid oxide electrolyte fuel cell generator, for generating electrical power. However, the direct use of hydrocarbon fuels can result in carbon deposition within the generator apparatus partly due to hydrocarbon cracking. Carbon deposition tends to reduce the life of the components of the generator apparatus, such as the fuel cells, insulation boards, and reforming catalysts, which in turn reduces efficiency of the generator. To reduce carbon deposition, it is known to reform the natural gas or other hydrocarbon fuel gases into simpler molecules, namely into carbon monoxide (CO) and hydrogen ($h_2$), through the use of a reforming catalyst and added water vapor (steam) and/or carbon dioxide ($CO_2$) prior to introduction of the fuel gases into the fuel cell generator. The use of the CO and $H_2$ produced from reforming effectively provides the oxidizable fuel for the electrochemical fuel cells, and carbon deposition is thereby reduced or eliminated.

The presence of water vapor and/or carbon dioxide and a reforming catalyst, such as finely divided Ni or finely divided Ni plus MgO mixtures, allows the conversion of gaseous hydrocarbon fuels, typically natural gas comprising in most part methane ($CH_4$), to CO and $H_2$ by the endothermic reforming reaction which is typically performed at about 600° C. to 900° C. The reforming reactions for methane are represented by Equations (1) and (2).

$$CH_4 + H_2O(g) \leftrightarrows 3H_2 + CO \quad (1)$$

$$CH_4 + CO_2 \leftrightarrows 2H_2 + 2CO \quad (2)$$

The reformed fuel is then combined, for example, in a high temperature, solid oxide fuel cell generator, with an oxidant, such as air or $O_2$, to produce electrical energy and heat. If the reforming reaction has insufficient oxygen in the form of $H_2O$ (steam) and $CO_2$, undesirable carbon deposition will occur partly due to hydrocarbon cracking. A typical natural gas fueled, high temperature, solid oxide electrolyte fuel cell generator should operate with atomic ratios of O:C in the range of about 2.0:1 to 2.5:1 prior to reforming, to avoid carbon deposition.

Systems which reform natural gas or other hydrocarbon gases could be made more effective by controlling and maintaining the O:C ratio at a value sufficient to prevent the deposition of carbon in the system. However, a useful device to monitor the O:C ratio at the elevated temperatures of the hydrocarbon reformer, especially in an internal reformer of a high temperature, solid oxide electrolyte fuel cell generator, has not been taught. It would be desirable to provide a useful device to assist in monitoring O:C ratios of a reformable fuel gas mixture prior to reforming.

An electrochemical cell can be used as an oxygen sensor. An oxygen sensor based on a solid oxide electrolyte electrochemical cell is taught, for example, in U.S. Pat. No. Res. 28,792 (Ruka, et al.). At elevated temperatures, a potential difference is developed between the electrodes of the electrochemical cell, due to differences in oxygen partial pressures between a sample and a reference atmosphere across a solid electrolyte disposed between two electrodes, i.e., a cathode and an anode. This potential difference at a known temperature and reference oxygen partial pressure is coupled to an external electrical circuit which relates this potential difference to the oxygen partial pressure of the sample atmosphere contacting the electrochemical cell functioning as an oxygen sensor. The oxygen sensor thereby encodes oxygen partial pressure in a manner that can be used for monitoring and control purposes.

The pertinent electrochemical reaction at the cathode of the oxygen sensor where air is typically used as the reference gas is represented by Equation (3).

$$O_2 + 4e^- \leftrightarrows 2O^{2-} \quad (3)$$

The electrochemical reaction at the anode of the oxygen sensor where the oxygen partial pressure is typically lower is represented by Equation (4).

$$2O^{2-} \leftrightarrows O_2 + 4e^- \quad (4)$$

For calibration, in Ruka, et al., one of the electrodes of the electrochemical cell is used as a reference electrode over which flows an atmosphere with known oxygen partial pressure and total overall pressure. An oxygen containing atmosphere to be measured of known total pressure is exposed to the other electrode which can be termed the measurement or sensor electrode. The measured potential difference between the electrodes is used to calculate the unknown partial pressure of the oxygen at the sensor electrode and, thus, the oxygen concentration of the oxygen containing sample atmosphere.

Other gas sensor designs are taught in U.S. Pat. Nos. 4,377,460 (Hirayama, et al.), 4,391,690 (Lin, et al.), and 4,902,401 (Lin, et al.). These gas sensors are similarly solid electrolyte electrochemical cells which sense the equilibrium of a gas species of interest and generate an electromotive force (EMF) signal that represents the difference in partial pressure of the gas species across the ion conductive solid electrolyte sensor disposed between two electron conductive electrodes. The monitored gas stream contacts a sensor electrode while the opposite electrode serves as a reference electrode which is contacted with a reference gas stream. Conventional solid electrolyte compositions require operating temperatures typically between 200° C. and 1000° C. to exhibit the desired and almost exclusive ion conductivity of the solid electrolyte to generate a suitable EMF signal.

The EMF signals generated by an oxygen gas sensor are developed in accordance with the well-known Nernst equation represented by Equation (5).

$$EMF = \frac{RT}{mF} \ln \frac{P_{O_2}}{P^1{}_{O_2}}, \text{ for the } O_2 \text{ cell,} \quad (5)$$

where R=Universal Gas Constant; T=Absolute Temperature (°K); F=Faraday Constant; P=Partial Pressure of Reference Gas; $P^1$=Partial Pressure of Monitored Gas; and, m=Number of Electrons Transferred=4 electrons per $2O^{2-}$ for the $O_2$ cell. From this equation and with knowledge of the oxygen partial pressure on the reference side and temperature, a direct measurement of the $O_2$ gas partial pressure in the monitored gas environment on the measurement side can be made by measuring the EMF of the sensor cell or cells. The EMF can be used to drive a meter or a control circuit, or the level can be digitized or otherwise encoded as needed.

High temperature, solid oxide electrolyte fuel cells and multi-cell generators and configurations thereof designed for converting chemical energy into direct current electrical energy, typically in a temperature range of from 600° C. to 1200° C., are well known, and taught, for example in U.S. Pat. Nos. 4,395,468 (Isenberg) and U.S. Pat. No. 4,490,444 (Isenberg). There, a previously reformed hydrocarbon fuel converted to either $H_2$ or CO is fed into the generator apparatus at one end and flows parallel to the exterior fuel electrode surfaces of the fuel cells. Spent fuel is combusted with spent oxidant to release heat and then exits the generator apparatus.

Other high temperature, solid oxide electrolyte fuel cells are known where spent fuel containing $H_2O$ and $CO_2$ is recirculated and mixed with a fresh gaseous hydrocarbon fuel at an ejector, nozzle or the like in the interior of the generator apparatus. The gaseous mixture is then fed through an internal catalytic hydrocarbon reformer to produce a reformed fuel gas, such as $H_2$ and CO, which is fed to contact the exterior fuel electrode surfaces of the fuel cells in the generator apparatus, as taught in U.S. Pat. No. 4,729,931 (Grimble). Other high temperature, solid oxide electrolyte fuel cell generator apparatus having internal catalytic hydrocarbon reformers are taught in U.S. Pat. No. 4,729,931 (Grimble); U.S. Pat. No. 4,983,471 (Reichner, et al.); U.S. Pat. No. 5,047,299 (Shockling); U.S. Pat. No. 5,082,751 (Reichner) U.S. Pat. No. 5,143,800 (George, et al.); and, U.S. Pat. No. 5,169,730 (Reichner, et al.).

Use of recirculated spent fuel gases produced from electrochemical operations in an electrochemical generator apparatus, such as a solid oxide fuel cell generator, to provide the oxygen species required for hydrocarbon reforming, namely gaseous $H_2O$ and/or $CO_2$, for combination with gaseous fresh hydrocarbon feed fuel to produce a reformable gas mixture, e.g., by means of an ejector or aspirator powered by the inlet fresh hydrocarbon feed fuel pressure, potentially has several problems. The reformable gas mixture, however, must be closely regulated to provide proper generator operations and eliminate carbon deposition. To address certain problems, the O:C ratios of the feed gas entering a reforming chamber should be optimally monitored and controlled to maintain desired levels. In this manner, it is possible to reduce or eliminate unwanted carbon deposition that may occur when the ratio is improper. In practical applications, the composition of the fresh hydrocarbon feed fuel gas typically may vary, requiring control of the amount passing through the ejector, and also control of the amount of water vapor and/or carbon dioxide laden spent fuel gas. For example, too great a draw of spent fuel gas at the ejector, will reduce the Nernst potential in a significant portion of the generating chamber of the apparatus and will result in lower operating voltage or poorer utilization of fuel than would otherwise be possible.

However, it is not currently possible to effectively monitor and control O:C ratios of a feed gas entering a reforming chamber of an electrochemical generator with a conventional high temperature electrochemical cell functioning as an oxygen gas sensor, since system noise, e.g., temperature variations and sample gas concentration variations, destroy any meaningful EMF readings. Therefore, it would be advantageous to monitor the reformable gas mixture entering or exiting the reforming chamber by a novel and a substantially noise-free gas sensor to facilitate optimal hydrocarbon reforming, and prevent carbon deposition and insure proper recirculation rate of spent fuel gas.

What is needed is a gas sensor that can effectively monitor, preferably on-line, the O:C ratios of the inlet or outlet fuel gas streams of the reformer such as a reformer of a high temperature, solid oxide electrolyte fuel cell generator. Such an oxygen gas sensor coupled to the appropriate control equipment would prevent carbon deposition and prevent reduction in electrochemical generator efficiency.

SUMMARY OF THE INVENTION

It is an object of the invention to provide a gas sensor to assist in monitoring gas concentrations of gas mixtures containing gaseous hydrocarbons and gaseous $H_2O$ and/or $CO_2$.

It is another object of the invention to provide an oxygen sensor to monitor $O_2$ content of gas mixtures containing gaseous hydrocarbons and gaseous $H_2O$ and/or $CO_2$.

It is yet another object of the invention to provide an on-line oxygen sensor at the inlet of or at the exit of a hydrocarbon reformer, to effectively monitor O:C atomic ratios of a reformable hydrocarbon feed gas mixture.

It is a further object of the invention to provide an electrochemical generator apparatus, such as a high temperature, solid oxide fuel cell generator, having an internal hydrocarbon reformer coupled with an on-line oxygen sensor to assist in monitoring O:C atomic ratios of a reformable hydrocarbon feed gas.

It is a feature of the invention to control and maintain a constant temperature in the area of the gas sensor electrodes and electrolyte in order to reduce system noise.

It is another feature of the invention to feed a monitored gas to the gas sensor that is at chemical equilibrium in order to reduce system noise.

It is yet another feature of the invention to provide a compact gas sensor that can be positioned close to the interior of an electrochemical generator, such as a high temperature, solid oxide fuel cell generator.

The invention resides in a gas sensor for measuring the effective $O_2$ content of a monitored gas environment containing oxygen and carbon characterized by a housing positioned in a monitored gas environment, the housing including an inlet to enable a monitored gas to enter the housing, and further including its own internal catalytic hydrocarbon reforming chamber containing a reforming catalyst, typically Ni and MgO, within the housing and adjacent to the monitored gas inlet, the reforming chamber having an inlet to enable the monitored gas environment to enter the reforming chamber and an outlet to enable the monitored gas to exit the reforming chamber, and even further including a solid oxide electrolyte electrochemical cell within the housing and adjacent to the outlet of the reforming chamber, the solid oxide electrolyte electrochemical cell including a solid oxide electrolyte, typically yttria stabilized zirconia, disposed between an exterior sensor electrode, typically platinum, exposed to the monitored gas environment and an interior reference electrode, typically platinum, isolated from said monitored gas environment and exposed to a reference gas environment at a known oxygen partial pressure, heating means, typically a furnace with closely controlled temperature, in heat communication with the reforming chamber and electrochemical cell, and circuit and voltage measuring means connected between the sensor electrode and the reference electrode to measure and display the potential difference between the two electrodes as a measure of the effective $O_2$ partial pressure of the monitored gas which can be correlated to an O:C ratio of the monitored gas and accordingly adjusted to a desired O:C ratio by appropriate means.

The invention further resides in an electrochemical generator apparatus used for generating electrical energy, such as a high temperature, solid oxide electrolyte fuel cell generator, having an on-line gas sensor for measuring $O_2$ content of a fuel mixture containing oxygen and carbon to electrochemical fuel cells, where the generator comprises a fresh gaseous hydrocarbon feed fuel inlet, a gaseous feed oxidant inlet, a gaseous spent fuel recirculation channel, a combustion chamber, a reforming chamber containing a reforming catalyst, a generator chamber positioned between the combustion chamber and the reforming chamber, the generator chamber containing a plurality of electrochemical fuel cells, each cell having an exterior fuel electrode and an interior air electrode and a solid electrolyte positioned therebetween, where the spent recirculation channel passes from the generator chamber to combine with the fresh gaseous hydrocarbon feed fuel inlet at a mixing apparatus and a reformable fuel mixture exits the mixing apparatus and passes the reforming chamber to be reformed to a useful fuel to pass to the generator chamber and over the fuel electrode of the fuel cells to generate electrical energy, and characterized by having a portion of either the reformable gas mixture entering the reforming chamber or the reformed gas mixture exiting the reforming chamber pass through an oxygen gas sensor, the gas sensor comprising a tubular housing positioned in communication with the monitored fuel gas mixture environment having an inlet to enable a small portion of the fuel gas mixture to enter the tubular housing, a small catalytic hydrocarbon reforming chamber containing a reforming catalyst positioned within the tubular housing having an inlet to enable said monitored fuel gas mixture to enter said reforming chamber and an outlet to enable said monitored gas to exit said reforming chamber, a solid electrolyte electrochemical cell positioned within said housing at said reforming chamber outlet, said solid electrolyte electrochemical cell including a solid electrolyte disposed between a sensor electrode exposed to said monitored fuel gas mixture and a reference electrode isolated from said monitored fuel gas mixture environment and exposed to a reference gas environment at a known oxygen partial pressure; heating means in heat communication with the oxygen gas sensor, and, circuit and voltage measuring means connected between the sensor electrode and the reference electrode to measure and display the potential difference between the two electrodes as a measure of the partial pressure of the monitored gas and accordingly to help determine the O:C ratio of the fuel mixture in order to adjust the O:C ratio to a desired ratio to avoid carbon deposition. The electrochemical generator can further include valve means to adjust the flow of the fresh hydrocarbon feed fuel to the spent fuel and control the O:C ratio entering said reforming chamber of said electrochemical generator apparatus. The oxygen gas sensor is preferably compact and can be positioned in an area close to or within the electrochemical generator apparatus.

The invention also resides in a method to assist in monitoring O:C atomic ratios of a fuel mixture prior to entering a generator chamber of a high temperature, solid oxide electrolyte fuel cell generator, characterized by the steps of: (A) providing a fuel gas mixture comprising hydrocarbons and $H_2O$ and/or $CO_2$; (B) passing the fuel gas mixture to be monitored through an oxygen gas sensor as described above; (C) providing an oxygen reference gas at a known partial pressure to the reference electrode; (D) measuring the EMF which is a function of the ratio of oxygen partial pressures of the reformable fuel mixture and the reference gas; (E) correlating the EMF to a given O:C ratio; and, (F) adjusting the ratio of O:C in the fuel mixture to a desired ratio.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

Figures 1A, 1B:
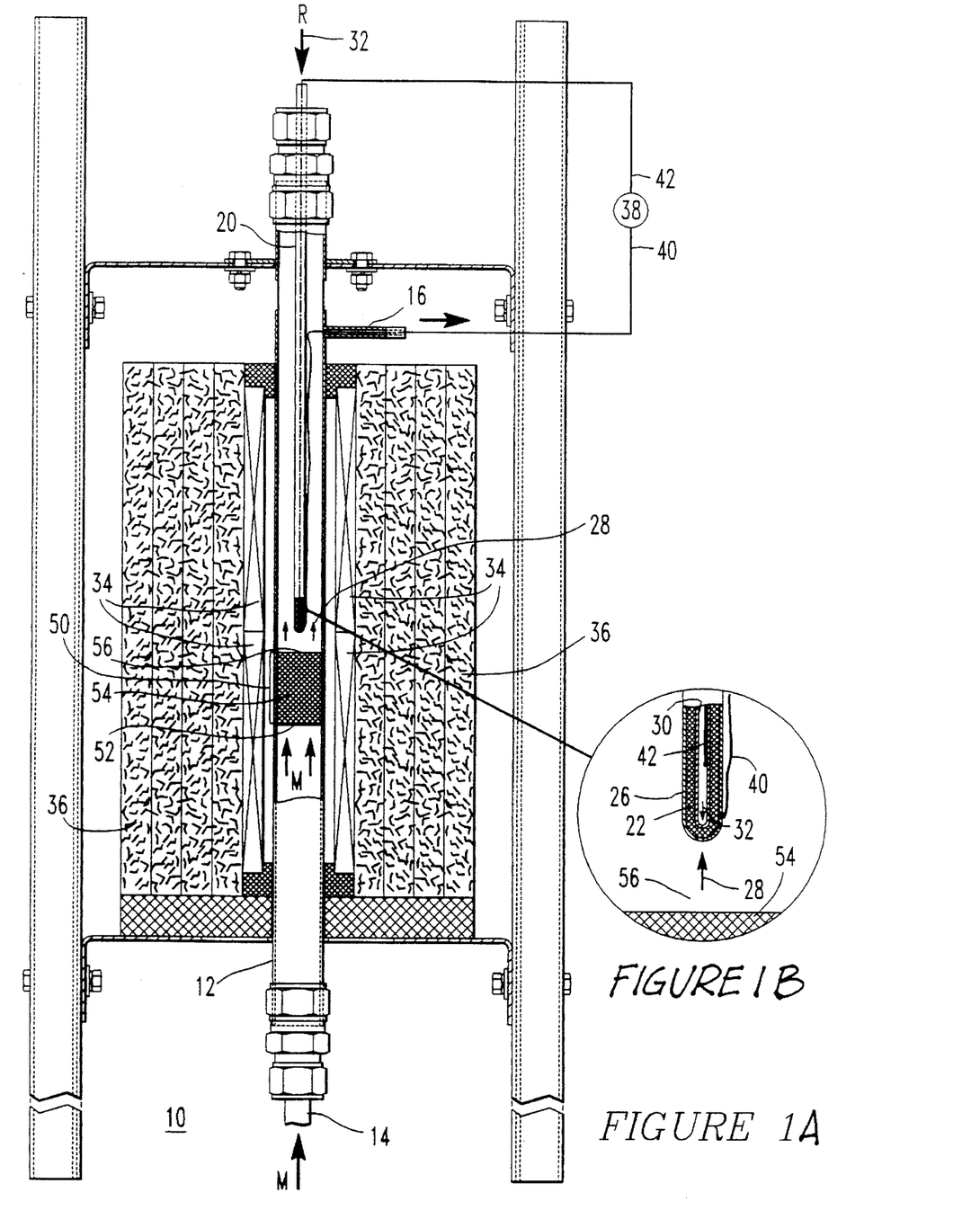
FIGS. 1A and 1B is an illustration of an oxygen gas sensor for monitoring oxygen partial pressures of gas mixtures containing hydrocarbons according to the invention.

Referring now to FIGS. 1A and 1B, a gas sensor 10 according to the invention is shown. According to the invention as shown, a monitored gas, as indicated by M, such as a mixture of hydrocarbons (e.g. natural gas) and $H_2O$ (steam) and/or $CO_2$ along a flowpath of an electrochemical power generator including a hydrocarbon reformer, is directed to the gas sensor 10 for monitoring. The gas sensor 10 includes a housing 12 that has an inlet end 14 through which the monitored gas M is directed to enter for measurement, and an outlet end 16 through which the monitored gas is exhausted back into the system. The housing 12 can be made of a high temperature resistant material such as Inconel metal or alumina for long term operation. Preferably, the inside walls of the housing 12 includes surfaces exposed to the hydrocarbon monitored gas M that are coated with a layer of catalytic reforming material, such as Ni and MgO or the like, as taught in U.S. Pat. No. 4,898,792 (Singh, et al.), which is incorporated by reference herein. The reforming catalyst along the walls of the housing of the gas sensor operates in a manner similar to the reforming catalyst of an electrochemical generator of which the gas sensor can be a part to prevent carbon formation on the gas sensor components. It should be understood that the housing can be tubular, rectangular, or other configurations, and is coupled by appropriate fittings to extract, measure and return the monitored gas to the system if desired.

Partially contained within the tubular housing 12 of the gas sensor 10 of the invention is a solid electrolyte electrochemical cell or gas sensor cell 20 for monitoring the oxygen concentration of a gas species contained within the monitored gas environment, after passing through the small internal, self-contained reformer unit. The monitored oxygen partial pressure is measured by generating an electrical signal or electromotive force (EMF) that varies with the partial oxygen pressure changes of a gas species involved in the electrochemical reactions of the cell 20. The two electrodes of the electrochemical cell 20 are respectively exposed to the gas environment with unknown oxygen partial pressure to be monitored, to a reference gas environment at a partial pressure that is accurately known and preferably constant, and to a temperature that is accurately known and preferably constant. Thus, the EMF of the electrochemical cell output varies with variations in the oxygen partial pressure of the monitored gas. A detailed description of the operation of a solid electrolyte electrochemical cell gas sensor suitable for oxygen gas concentration measurements is provided in U.S. Pat. No. Re. 28,792 (Ruka, et al.), which is incorporated by reference herein.

The electrochemical cell 20 includes a solid electrolyte 22 that is preferably made of nonporous stabilized zirconia, preferably $ZrO_2$ doped with yttria, preferably $Y_2O_3$. The solid electrolyte 22 is designed to have a high degree of ion conductivity relative to electronic conductivity. The preferred solid electrolyte 22 composition is $(ZrO_2)_{0.9}(Y_2O_3)_{0.1}$. The electrolyte can also be zirconia or hafnia stabilized by calcia or rare earths such as ytterbia which have stable $3^+$ valences. The solid electrolyte 22 exhibits ion conductivity at elevated temperatures suitable to generate an electrical signal or EMF indicative of the oxygen partial pressure of the monitored gas environment. The solid electrolyte 22 is secured to or integrally formed from a closed-end gas sensor cell 20 that may be tubular and is positioned within the housing 12. This solid electrolyte, electrochemical, closed end gas sensor cell 20 is preferably integral with the solid electrolyte 22, but can also have a separate porous support structure (not shown) to which the solid electrolyte is secured. The gas sensor cell 20 provides sealing or isolation between a sensor electrode 26 and a reference electrode 30 to isolate the two electrodes which are positioned in two different gas environments, a monitored gas environment and a reference gas environment, respectively.

The sensor electrode 26 is positioned in intimate contact with a surface of the solid electrolyte 22 and is also exposed to the monitored gas environment, as shown by arrow 28. The open end 14 of the housing 12 enables the monitored gas M to enter the housing 12 and to contact the sensor electrode 26. The sensor electrode 26 preferably comprises a thin layer of porous electrically conductive material, such as platinum (Pt) metal or alloy. The reference electrode 30 is positioned in intimate contact with the opposite surface of the solid electrolyte 22 and also in contact with the reference gas environment, as shown by arrow 32. The reference electrode 30 likewise preferably comprises a thin layer of porous electrically conductive material, such as platinum (Pt) metal or alloy. The reference electrode 30 is isolated from the sensor electrode 26 by the electrolyte 22 thereby forming the electrochemical, gas sensor cell or 20 contained within the housing 12. The gas sensor cell 20 also includes a closed-end at the electrode-electrolyte interfaces and a reference gas inlet end remote from the housing inlet 14 to permit a reference gas R or 32 to enter the electrochemical cell 20 and contact the reference electrode 30. A reference gas 32, such as air for the $O_2$ gas sensor, having a known concentration and oxygen partial pressure is supplied from a reference gas source (not shown), such as a compressor, for contact with the reference electrode 30. It should be understood that the sensor electrode and reference electrode can be positioned at the lowermost closed-end portion of the electrochemical cell 20 and can also extend a distance from the closed-end as shown.

In order to maintain the partial pressure of the reference gas environment 32, it is necessary to effectively seal the, tubular gas gauge 20 within the housing 12 so as to avoid leakage of the monitored gas environment M into the reference gas environment 32. The sealing can be effectively performed by standard compression seals such as Swagelok fittings.

Moreover, the solid electrolyte electrochemical cell 20 disposed within the housing 12 is arranged in thermal transfer contact with a heat source or furnace 34 that maintains a predetermined operating temperature, preferably at temperatures between 600° C. and 1000° C., more preferably at temperatures between 700° C. and 950° C. The operating temperature of the gas sensor cell 20 is carefully held constant to eliminate cell temperature variation as a variable in the Nernst equation, and consequently reduce system noise. It is an advantage of the invention to provide heating means to carefully control a constant temperature in the area of the gas sensor electrodes which eliminates EMF signal variations as a result of temperature changes in the gas monitoring operations. In addition, the elevated operating temperature is selected to provide suitable ionic conductivity of the solid electrolyte 22, typically yttria stabilized zirconia. The heat source 34 is further provided to reform the monitored gas before contacting the gas sensor cell 20. The housing 12 is preferably contained within an insulating material 36 in order to maintain the temperature.

The preferred gas sensor cell 20 assembly of the solid electrolyte gas sensor for an $O_2$ gas monitored environment can be represented by (6).

$O_2$Reference Gas (32),
    Pt/$ZrO_2 \cdot Y_2O_3$/Pt, $O_2$Monitored Gas 0 (M)     (6)

The electrochemical reactions for an $O_2$ concentration cell occurring at the electrode-electrolyte interfaces are represented by Equations (7) and (8).

$O_2 + 4e^- \leftrightarrows 2O^{2-}$ (cathode)     (7)

$2O^{2-} \leftrightarrows O_2 + 4e^-$ (anode)     (8)

At a given temperature, where the oxygen partial pressure of the reference gas and temperature are constant, the electrical output or EMF signal developed by the solid electrolyte electrochemical cell 20 is solely a function of the oxygen partial pressure in the monitored gas environment 28 that contacts the sensor electrode 26. Therefore, the oxygen partial pressure can be determined from the EMF output signal of the sensor. The EMF signal developed by the solid electrolyte electrochemical cell 20 is converted to oxygen partial pressure by calculation in accordance with the well-known Nernst Equation (5), as more completely described above.

$$EMF = \frac{RT}{mF} \ln \frac{P_{O_2}}{P^1_{O_2}}, \text{ for the } O_2 \text{ cell} \quad (5)$$

The EMF signal is developed by the gas sensor electrochemical cell 20 changes in response to the equilibrium partial pressure of oxygen in the gas of interest, as measured between the sensor electrode 26 and the reference electrode 30. The EMF is monitored by an external EMF measuring circuit 38. The measuring circuit 38 is electrically connected by electrical leads 40, 42 to the sensor electrode 26 and the reference electrode 30, respectively. The electrical leads are preferably made of platinum (Pt) metal. The EMF signal measured by circuit 38 is an indication of the equilibrium oxygen partial pressure of the monitored gas environment at the temperature of the $O_2$ gas sensor. The signal can be coupled to a controller arranged to adjust the positions of valves, the power level of compressors or other feed means, etc., which adjust the mixture of the monitored gas before it arrives at its desired destination, such as to a reformer of a high temperature, solid oxide electrolyte electrochemical fuel cell generator. The signal can also be digitized and used by a processor (not shown) to effect digital control, logging for data recording, etc.

Since the EMF signal of the gas sensor is sensitive to the equilibrium oxygen partial pressure of the gas species present in the gas to be monitored and to the temperature of the electrolyte 22, it is advantageous that chemical reactions, such as hydrocarbon reforming, should not occur on the sensor electrode 26 which can cause undesirable system noise. To ensure that the monitored gas M, typically a reformable gas mixture of hydrocarbons, such as natural gas comprising mostly methane ($CH_4$), and $H_2O$ and/or $CO_2$, is in a state of chemical equilibrium, i.e., completely reformed to CO and $H_2$, and is at the same temperature as the sensor electrode 26, it is important to completely reform the monitored gas M prior to contacting the gas sensor cell 20.

Accordingly, in the invention, the solid electrolyte electrochemical cell 20 is disposed in communication with an integral catalytic hydrocarbon reforming chamber 50. The reforming chamber 50 is also positioned in the housing 12. Reforming chamber 50 is disposed between the housing inlet 14 coupled to the monitored gas environment and the solid electrolyte electrochemical cell 20 contained within the housing. The reforming chamber 50 has an inlet end 52 to carry the monitored gas M to enter and contact a reforming catalyst 54 contained in the reforming chamber 50 and an outlet end 56 to carry the reformed monitored gas 28 to exit the reforming chamber 50 and to contact with the sensor electrode 26 of solid electrolyte electrochemical cell 20. The reforming catalyst 54 can be nickel or other well known useful reforming material for hydrocarbon gas into CO and $H_2$. Preferably, the reforming catalyst 54 within the reforming chamber is made of nickel fiber felt pads impregnated with an MgO plus nickel mixture or contains a packed bed of alumina pellets coated with catalytic nickel (Ni) and magnesium oxide (MgO).

The reformable monitored gas M, which is a mixture of gaseous hydrocarbons and gaseous $H_2O$ and/or $CO_2$, enters the housing 12 at housing inlet 14 and is first reformed, i.e., converted to CO and $H_2$, through the use of a reforming catalyst such as Ni and MgO, in the reforming chamber 50 contained within the housing prior to contacting the electrochemical gas sensor cell 20 also contained within the housing. For example, where the monitored gas M is a mixture of gaseous hydrocarbons, such as methane, and gaseous $H_2O$ and/or $CO_2$, the reforming reactions are given by Equations (9) and (10).

(9)

(10)

The reforming reaction is endothermic and, therefore, requires a supply of heat that can also be furnished by the heat source 34. To achieve complete conversion of the hydrocarbon fuel, the reforming reactions are best performed at temperatures in the range of 700° C. to 900° C. The $O_2$ sensor assists in monitoring the atomic ratios of $H_2O$ (steam) and/or $CO_2$ : gaseous hydrocarbon or O:C ratios in the oxygen sensor device according to the invention such that a desired O:C ratio can be adjusted and maintained in the monitored gas environment prior to entering the catalytic hydrocarbon reformer required by the fuel cell to eliminate hydrocarbon cracking and carbon deposition in the monitored system.

At chemical equilibrium, the partial pressure of oxygen in a monitored gas stream containing only compounds of hydrogen, carbon, and oxygen, is a function of the ratio of oxygen to carbon (O:C) in the mixture, the ratio of hydrogen to carbon (H/C) in the mixture, and the temperature of the mixture. At chemical equilibrium the oxygen partial pressure of the monitored gas stream is a function only of the O:C ratio, if the H/C ratio and the temperature of the gas stream are fixed at known values. In a high temperature solid oxide fuel cell generator, the H/C ratio is constant throughout the fuel stream side, and is equal to the H/C ratio of the incoming fuel. If the equilibrium temperature of the monitored gas stream is also known and closely controlled, such as with an electric heater 34 surrounding the reformer 50 of the gas sensor 10 so that the gas reaches equilibrium inside the gas sensor reformer 50, then the oxygen partial pressure of the monitored gas is a function only of the O:C ratio of the monitored gas. Then, the O:C ratio of the monitored gas may be calculated from the measured potential difference across the electrodes of the gas sensor 20, since the oxygen partial pressure of the monitored gas can be determined from the potential difference across the electrodes, and the oxygen partial pressure of the monitored gas at equilibrium is a function only of the O:C ratio of the monitored gas if the H/C ratio and the temperature of the gas are both known.

Figure 2:
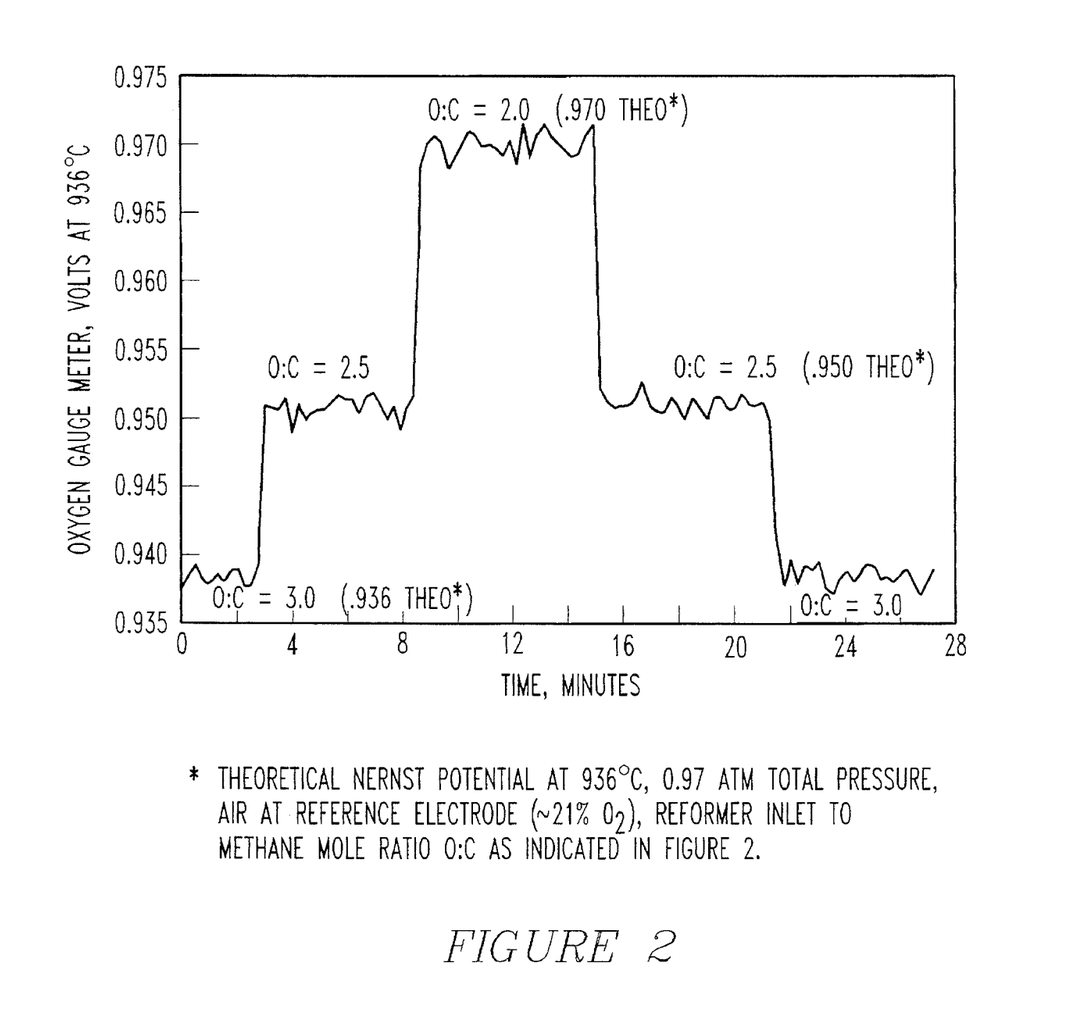
FIG. 2 is a graph of voltage outputs for different O:C ratios of a given gas system using an oxygen gas sensor according to the invention.

In operation, the reformable monitored gas M is fed through the housing inlet 14 and first passes the reforming chamber 50 where the hydrocarbons and $H_2O$ and/or $CO_2$ of the monitored gas are converted to $H_2$ and CO. After passing through the reforming chamber 50, the reformed gas, now consisting of $H_2$, CO, $CO_2$, $H_2O$ and very small amounts of unreformed hydrocarbon species, contacts sensor electrode 26 which is in communication with the solid electrolyte 22 and the reference electrode 30 of the gas sensor cell 20, and then exits the housing at outlet 16 as spent monitored gas. The spent monitored gas is preferably returned to the monitored gas stream at some point upstream of its intended point of use. The reference electrode 30 is exposed continuously to a reference gas 32 and serves as a known partial pressure reference. Thus, the EMF signal generated across the electrochemical cell or gas gauge 20 is a measure of the oxygen partial pressure of the monitored reformed gas. The EMF signal can, if desired, be fed to a control system (not shown) which readjusts the monitored feed gas M composition to the desired ratios. By way of example, FIG. 2 is an example of data obtained using the gas sensor device of the invention which shows the stable voltage output for different steam to carbon (O:C) ratios of a test gas stream simulating a reformer input reformable gas mixture.

According to another aspect of the invention, the synergistic combination of an internal catalytic hydrocarbon reformer 50, heating means 34, gas sensing electrochemical cell 20 disposed in a single housing 12 to form the gas sensor, preferably an oxygen gas sensor, of the invention is particularly useful to monitor O:C atomic ratios of hydrocarbon feed fuel gas compositions in a high temperature, solid oxide fuel cell apparatus prior to entering or after exiting the internal hydrocarbon reformer of the fuel cell apparatus. High temperature, solid oxide fuel cell configurations, materials of construction, and fuel gas compositions are taught in U.S. Pat. Nos. 4,395,468 (Isenberg); U.S. Pat. No. 4,490,444 (Isenberg); U.S. Pat. No. 4,562,124 (Ruka); and, U.S. Pat. No. 4,751,152 (Zymboly), which are incorporated by reference herein in their entireties. Moreover, high temperature, solid oxide electrolyte fuel cell generator apparatus containing internal catalytic hydrocarbon reformers are taught in U.S. Pat. Nos. 4,729,931 (Grimble); U.S. Pat. No. 4,983,471 (Reichner, et al.); U.S. Pat. No. 5,047,299 (Shockling); U.S. Pat. No. 5,082,751 (Reichner); U.S. Pat. No. 5,143,800 (George, et al.); and U.S. Pat. No. 5,169,730 (Reichner, et al.), which are incorporated by reference herein in their entireties.

The oxygen gas sensor of the invention provides an effective method to assist in monitoring the O:C ratios in a fuel mixture fed to a high temperature, solid oxide electrolyte fuel cell generator, and accordingly facilitates adjustments to desired O:C ratios in order to avoid carbon deposition in the generator. Systems which reform natural gas or other hydrocarbon gases advantageously are operated using an O:C ratio sufficient to prevent the deposition of carbon in the system. And until the gas sensor of the present invention, there has not been an effective high temperature method of and apparatus for monitoring O:C ratios used in a reformer, especially in an internal reformer of a high temperature, solid oxide electrolyte fuel cell generator. The gas sensor of the invention can be used to assist in monitoring the oxygen partial pressure of a gas atmosphere at the inlet or outlet of a hydrocarbon reformer and accordingly the O:C ratios of the reformer inlet gas composition in order to effectively control the ratios of O:C of the gas entering the reformer to avoid carbon deposition. A preferred atomic ratio of $H_2O$ (steam) to fresh hydrocarbon feed fuel or O:C atomic ratio is about 2.0:1 to 5:1, even more preferably about 2.1:1 to 3:1 for a natural gas fueled electrochemical generator.

Figure 3:
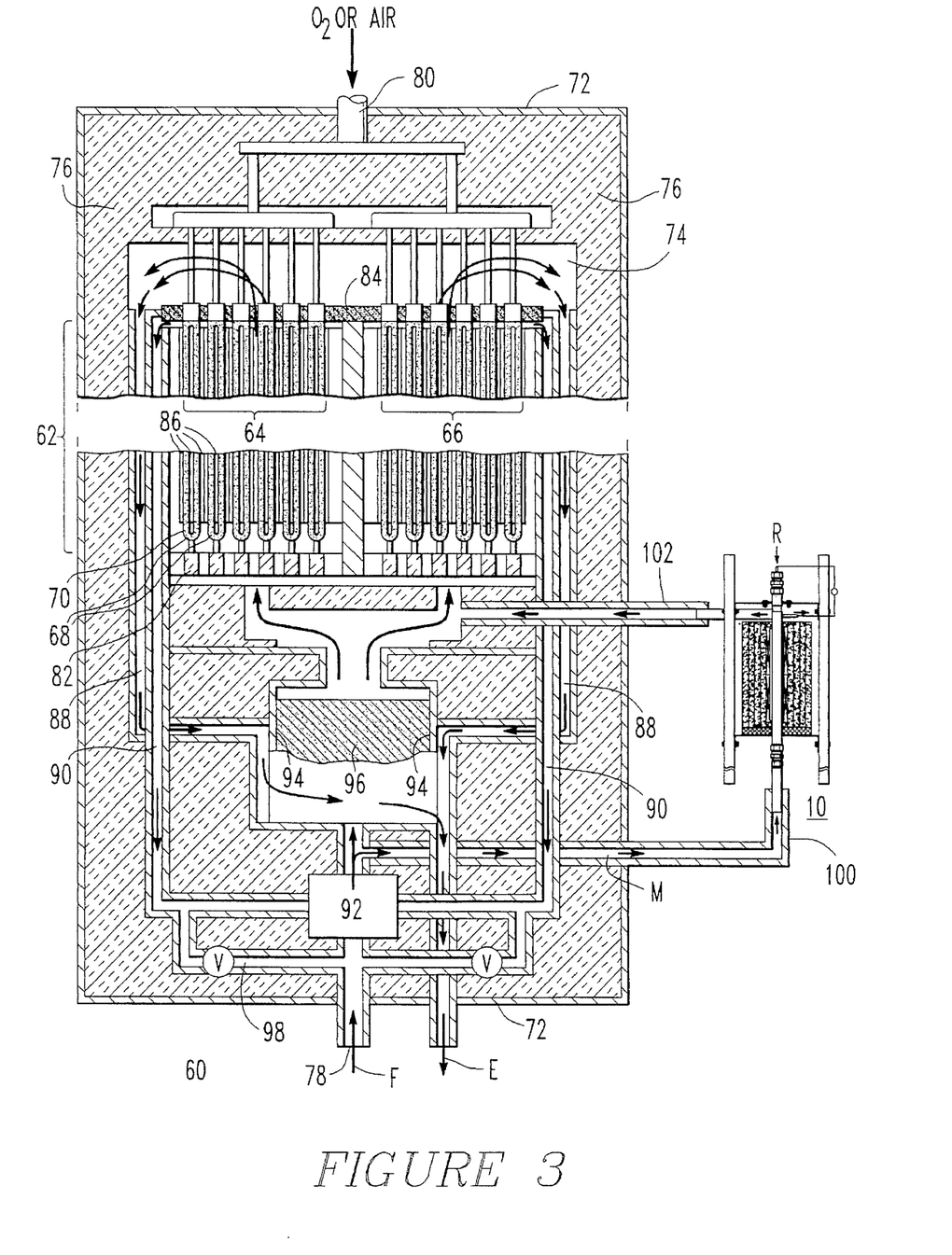
FIG. 3 is a side view of an electrochemical generator having a catalytic hydrocarbon reformer that also contains an on-line oxygen gas sensor for assisting in the monitoring of input reformer hydrocarbon feed gas content.

Referring now to FIG. 3, an electrochemical cell apparatus or generator 60 for generating electrical energy, such as a high temperature, solid oxide electrolyte fuel cell generator, is shown containing two cell bundles 64 and 66, each bundle containing a plurality of parallel, axially elongated electrochemical cells 68. The fuel cells 68 are located in generator chamber 62. Each fuel cell 68 has an exterior fuel electrode 70 covering its axially elongated surface, an interior air electrode (not shown), and a solid oxide electrolyte (not shown) between the electrodes, as is well known in the art. The air electrode is generally a doped ceramic of the perovskite family, for example, doped $LaMnO_3$. The solid electrolyte is generally yttria stabilized zirconia, and the fuel electrode 70 is generally a nickel-zirconia or cobalt-zirconia cermet material. An optional calcia stabilized zirconia support (not shown) for the air electrode can also be provided.

The electrochemical cell apparatus 60 will operate with an interior temperature in the range of about 600° C. to 1200° C. An outer housing 72, surrounds the entire apparatus. An inner housing (not shown) surrounds a plurality of chambers, including the generator chamber 62 and a combustion chamber 74, and is preferably comprised of a high temperature resistant metal such as Inconel. Thermal insulation 76, such as low density alumina insulation board is contained within the outer housing 72. Penetrating the outer housing and insulation is a fresh gaseous hydrocarbon feed fuel inlet 78 and a gaseous oxidant feed inlet 80, such as air or oxygen, as well as ports for electrical leads and the like (not shown). The generator chamber 62 extends between a perforated barrier 82 and a porous barrier 84. The porous barrier 84 need not be a sealed structure. The porous barrier, in particular, is designed to allow spent (depleted) fuel gas flow, between the generator chamber 62, operating at a pressure slightly above atmospheric, and the combustion chamber 74, operating at a slightly lower pressure, but still above atmospheric pressure. High temperature, elongated, solid oxide electrolyte fuel cells 68 extend between the combustion chamber 74 and the perforated barrier 82. The fuel cells have open ends in the combustion chamber 74, and closed ends in the generator chamber 62 near the perforated barrier. Each individual fuel cell 68 generates approximately one volt on open circuit, and a plurality are electrically interconnected through conducting felts 86, usually nickel fiber metal, preferably in a series-parallel rectangular array, as is well known.

By way of example, during operation, a gaseous feed oxidant, such as air or oxygen, as shown by O, is fed through oxidant feed inlet 80, and enters oxidant feed conduits at a temperature of approximately 500° C. to 700° C., and a pressure above atmospheric, being optionally heated prior to entering the housing by conventional means, such as a heat exchanger (not shown) coupled with a blower (not shown). The oxidant, within the conduits, is passed through the combustion chamber 74, where it is further heated to a temperature of approximately 800° C. to 900° C. by combusted exhaust gas. The oxidant then flows through the length of the oxidant circuit, through the conduits which extend down the inside length of the fuel cells, being further heated to approximately 1000 ° C. by virtue of absorbing most of the heat generated during the electrochemical reaction. A smaller fraction of the heat is absorbed by the fuel.

The oxidant is discharged into the closed end bottom of the fuel cells. The oxidant within the fuel cells reverses direction, and electrochemically reacts at the inner air electrode along the inside active length of the cells, depleting somewhat in oxygen content as it approaches the open ends of the fuel cells. The depleted or spent oxidant is then discharged into the combustion chamber through the open cell ends. This spent oxidant combusts with depleted or spent fuel (unoxidized), where part of the total depleted fuel passes through the porous barrier 84 to form combusted a hot combusted exhaust gas E, which exits the apparatus through a separate combusted exhaust gas exit channel 88. The combusted exhaust channel 88 can be made of a high temperature resistant metal, such as Inconel. The combusted exhaust channel 88 can be directed to heat the reforming material prior to exiting the generator apparatus, as shown.

A gaseous hydrocarbon feed fuel F that has not yet been reformed, such as a gaseous hydrocarbon, including hydrocarbons such as methane ($CH_4$,), ethane ($C_2H_6$), propane ($C_3H_8$)), and the like, vaporized petroleum fractions such as naphtha, and alcohols, such as ethyl alcohol ($C_2H_5OH$), and the like, and natural gas, that is, a mixture of 85% methane, and 10% ethane with a balance of propane, butane and nitrogen, can be used for electrochemical fuel. These reformable hydrocarbon fuel mediums are fed into the generator through fresh hydrocarbon feed fuel inlet 78.

A major portion of the hot gaseous spent fuel typically comprising $H_2O$ and $CO_2$, and also some $H_2$ and CO, formed along the axial length of the cells and not passed to the combustion chamber passes to a spent fuel recirculation channel 90, which can be made of a high temperature resistant metal such as Inconel. Another portion of the hot spent fuel passes into combustion chamber 74 as previously described, to combust with spent air, and preheat the fresh oxidant feed and reforming catalyst and exit through combusted exhaust channel 88. The spent fuel recirculation channel 90 passes from the generator chamber 62 to feed into and combine with the fresh hydrocarbon feed fuel inlet 78 at a circulation and mixing apparatus 92 which can be of any type known in the art, for example, an ejector, jet pump, aspirator, or the like, which is positioned in a cooler region of the insulation, as shown. The mixing apparatus 92 allows recirculation of a portion of the spent fuel fed in recirculation channel 90 to mix with the fresh feed fuel to provide a reformable fuel mixture which passes through a reformable fuel mixture channel en route to a reforming chamber 94.

The reformable fuel mixture will contain hydrocarbon feed fuel gas and at least water vapor (steam) and/or $CO_2$ and usually also some $H_2$ and CO, contributed by the spent fuel that enters the circulation mixing apparatus. The presence of water vapor and/or carbon dioxide plus a reforming catalyst 96, most commonly Ni and MgO, allows conversion of gaseous hydrocarbons to CO and $H_2$. The reformable fuel mixture then passes through the reforming chamber 94, shown half in section, containing reforming catalyst material 96, such as nickel and MgO, or other well known useful reforming material for fuel gas.

Additionally, the fresh hydrocarbon fuel feed inlet 78 has one or more by-pass channels 98 controlled by valves V so that fresh hydrocarbon feed fuel F can by-pass the aspirating portion of the mixing apparatus 92, and flow directly into the gaseous spent fuel recirculation channel 90. Each by-pass channel has appropriate valving means or other metering means to control the flow of fresh hydrocarbon feed fuel into the gaseous spent fuel recirculation channel. This allows control of the quantity of spent fuel gas recirculated through recirculation channel 90 into the mixing apparatus 92. Mixing apparatus 92 will usually contain a nozzle from which fresh hydrocarbon feed fuel will exit at a high velocity, thereby entraining and circulating the spent fuel gas from recirculation channel 90. The amount of by-pass flow through each by-pass channel can therefore be varied by the valve V or other metering means, allowing a reduction in the amount of spent fuel gas, and thus water vapor and/or $CO_2$, i.e. the oxygen species for reforming, entrained within the mixing apparatus, in order to assure that an appropriate $H_2O$:gaseous hydrocarbon, or O:C ratio is achieved under various operating conditions.

In the invention, a portion of the reformable fuel mixture with a known H/C ratio after passing the mixing apparatus 92 can be routed into a gas sensor channel 100 to pass a gas sensor 10 of the invention, as previously described herein and shown in FIG. 1, to monitor O:C ratios of the reformable fuel mixture entering the reforming chamber. The gas sensor 10 is compact and when used in conjunction with an electrochemical fuel cell generator 60, such as a high temperature, solid oxide fuel cell generator, can be positioned in the interior (not shown) or the exterior of the generator.

The gas sensor 10 as described above includes a housing positioned in contact with a monitored gas environment M (i.e., the reformable gas mixture) having an inlet to enable a monitored gas to enter said housing; a catalytic hydrocarbon reforming chamber containing a reforming catalyst positioned within the housing having an inlet to enable said monitored gas to enter said reforming chamber and an outlet to enable said monitored gas to exit said reforming chamber; a solid electrolyte electrochemical cell positioned within the housing at the outlet of the reforming chamber, the solid electrolyte electrochemical cell including a solid electrolyte disposed between a sensor electrode exposed to the monitored gas environment and a reference electrode isolated from said monitored gas environment and exposed to a reference gas environment; heating means for the gas sensor cell and reformer sections; and, circuit means connected between the sensor electrode and the reference electrode to generate an electrical signal as a measure of the oxygen partial pressure of the monitored gas.

After passing the gas sensor 10, the monitored mixture can be passed into the reformed fuel at the exit of the fuel cell reformer through the gas sensor exit 102. The gas sensor 10 may be positioned within the electrochemical generator apparatus to use the sensible heat from the electrochemical operations. If the oxygen sensor 10 is positioned external to the generator 60, then the sensor inlet and exit channels must be heated and/or insulated to prevent condensation of water vapor in the monitored gas stream into liquid water. Water condensation would lower the O:C ratio of the gas stream, thus changing the measured results and giving a false O:C ratio indication.

A more detailed description of high temperature, solid oxide electrolyte electrochemical fuel cells and multi-cell generators and the materials of construction and operations thereof is taught in U.S. Pat. No. 4,395,468 (Isenberg), U.S. Pat. No. 4,490,444 (Isenberg) which are hereby incorporated by reference herein in their entireties. Moreover, all of the above referenced U.S. patents throughout this specification are hereby incorporated by reference herein in their entireties.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

We claim:

1. An electrochemical, fuel cell generator apparatus (60) having an on-line gas sensor (10) for measuring oxygen partial pressure of a fuel mixture comprising gaseous hydrocarbons and oxygen containing compounds of $H_2O$ and $CO_2$ to the electrochemical cells (68) of the fuel cell generator, comprising:

a fresh gaseous hydrocarbon feed fuel inlet (78);

a gaseous feed oxidant inlet (80);

a gaseous spent fuel recirculation channel (90);

a combustion chamber (74);

a reforming chamber (94) containing a reforming catalyst (96);

a generator chamber (62) positioned between the combustion chamber and the reforming chamber, the generator chamber containing a plurality of electrochemical cells (68), each cell having an exterior fuel electrode (70) and an interior air electrode and a solid electrolyte positioned therebetween; where the spent recirculation channel passes from the generator chamber to combine with the fresh gaseous hydrocarbon feed fuel inlet at a mixing apparatus (92) and a reformable fuel mixture exits the mixing apparatus and passes the reforming chamber to reform the reformable fuel mixture to a reformed fuel to pass to the generator chamber; and, a gas sensor and coupling means for passing a portion of either the reformable fuel mixture or the reformed fuel to define a fuel mixture through a gas sensor, the gas sensor (10) comprising a housing (12) with an inlet (14) coupled to the fuel mixture environment causing said portion of the fuel mixture to enter said housing to define a monitored gas and an outlet (16), a catalytic hydrocarbon reforming chamber (50) containing a reforming catalyst (54) in said housing, the reforming chamber having an inlet (52) communicating with said monitored gas fuel mixture and an outlet (56); a tubular, close ended, solid electrolyte, electrochemical, gas sensor cell (20) in said housing at said reforming chamber outlet, said solid electrolyte electrochemical, gas sensor cell (20) comprising a solid electrolyte (22) disposed between a sensor electrode (26) exposed to said monitored gas fuel mixture and a reference electrode (30) isolated from said fuel mixture environment and exposed to a reference gas environment at a known partial pressure of oxygen; heating means (34) in heat communication with said oxygen gas sensor, and, circuit means (38) between said sensor electrode and said reference electrode to process an electrical signal developed between the electrodes, the electrical signal providing a measure of the partial pressure of oxygen of said monitored gas.

2. The electrochemical generator of claim 1, wherein said reformable fuel mixture to said reforming chamber is controlled by valve means to adjust the flow of the fresh hydrocarbon feed fuel to the spent fuel and control the O:C ratio entering said reforming chamber of said electrochemical generator apparatus responsive to the electrical signal.

3. The electrochemical generator of claim 1, wherein said fuel mixture entering said gas sensor is the reformable fuel mixture.

4. The electrochemical generator of claim 3, wherein said portion of the reformable fuel mixture that passes through said gas sensor exits into said reformed fuel channel of the generator.

5. The electrochemical generator of claim 1, wherein said electrochemical cell includes said exterior fuel electrode of porous nickel-zirconia cermet, said interior air electrode of porous lanthanum manganite, and said solid electrolyte of gas-tight yttria stabilized zirconia.

6. The electrochemical generator of claim 5, wherein said gas sensor includes said sensor electrode of platinum, said reference electrode of platinum, and said solid electrolyte of yttria stabilized zirconia.

7. The electrochemical generator of claim 1, wherein said gas sensor is positioned within said electrochemical generator.

8. A method to assist in monitoring O:C atomic ratios of a reformable fuel mixture to be conditioned prior to entering a generator chamber of a high temperature, solid oxide electrolyte fuel cell generator, comprising:

(a) providing a reformable fuel mixture (F) comprising hydrocarbons and $H_2O$ and/or $CO_2$;

(b) passing the reformable fuel mixture (F) as a monitored gas (M) through an oxygen gas sensor (10), said oxygen gas sensor comprising a housing (12) positioned within or exterior to a monitored gas environment having an inlet (14) to monitor a gas containing hydrocarbons and oxygen species to enter said housing, a catalytic hydrocarbon reforming chamber (50) containing a reforming catalyst (54) positioned within said housing having an inlet (52) for said monitored gas to enter said reforming chamber and an outlet (56) for said monitored gas to exit said reforming chamber, a tubular, close ended, solid electrolyte, electrochemical, gas sensor cell (20) positioned within said housing at said reforming chamber outlet, said solid electrolyte, electrochemical, gas sensor cell (20) including a solid electrolyte (22) disposed between a sensor electrode (26) exposed to said monitored gas environment and a reference electrode (30) isolated from said monitored gas environment and exposed to a reference gas environment (R), heating means (34) in heat communication with the reforming chamber and electrochemical cell, and, circuit means (38) connected between said sensor electrode and said reference electrode to process an electrical signal between the electrodes, the electrical signal providing a measure of the partial pressure of oxygen said monitored gas;

(c) providing an oxygen reference gas (R) at a known partial pressure of oxygen to the reference electrode; and, (d) measuring the EMF as a function of the ratio of the partial pressure of oxygen of the reformable fuel mixture to that of the reference gas.

9. The method of claim 8, further comprising:

(e) correlating the EMF to a given O:C ratio; and, (f) adjusting the ratio of O:C in the reformable fuel mixture to a set ratio.

* * * * *